US012270026B1

(12) United States Patent
Ellefson et al.

(10) Patent No.: US 12,270,026 B1
(45) Date of Patent: Apr. 8, 2025

(54) DIRECTED EVOLUTION METHOD FOR TEMPLATE-INDEPENDENT POLYMERASES

(71) Applicant: Ansa Biotechnologies, Inc., Berkeley, CA (US)

(72) Inventors: Jared Ellefson, Oakland, CA (US); Daniel Arlow, San Francisco, CA (US); Sebastian Palluk, Oakland, CA (US)

(73) Assignee: Ansa Biotechnologies, Inc., Emeryville, CA (US)

( * ) Notice: Subject to any disclaimer, the term of this patent is extended or adjusted under 35 U.S.C. 154(b) by 635 days.

(21) Appl. No.: 17/192,824

(22) Filed: Mar. 4, 2021

Related U.S. Application Data

(60) Provisional application No. 62/985,744, filed on Mar. 5, 2020.

(51) Int. Cl.
*C12N 15/10* (2006.01)
(52) U.S. Cl.
CPC .............................. *C12N 15/1058* (2013.01)
(58) Field of Classification Search
CPC .................................................. C12N 15/1058
USPC .............................................................. 506/1
See application file for complete search history.

(56) References Cited

U.S. PATENT DOCUMENTS

| 7,514,210 B2 | 4/2009 | Holliger et al. |
| 7,691,576 B2 | 4/2010 | Holliger et al. |
| 8,932,831 B2 | 1/2015 | Korfhage et al. |
| 9,175,340 B2 | 11/2015 | Liu et al. |
| 2014/0308730 A1 | 10/2014 | Nikiforov et al. |
| 2015/0086981 A1 | 3/2015 | Cherkasov et al. |
| 2015/0284786 A1 | 10/2015 | Shapero et al. |
| 2018/0223321 A1 | 8/2018 | Makarov et al. |

FOREIGN PATENT DOCUMENTS

| WO | WO-0162983 A1 * | 8/2001 | ......... C12N 15/1034 |
| WO | 2004092331 A2 | 10/2004 | |
| WO | WO-2005045072 A1 * | 5/2005 | ......... C12N 15/1075 |
| WO | 2007070542 A2 | 6/2007 | |
| WO | 2014142981 A1 | 9/2014 | |
| WO | 2017190018 A1 | 11/2017 | |

OTHER PUBLICATIONS

Larsen et al. A general strategy for expanding polymerase function by droplet microfluidics. Nature Communications. 7, 2016, 1-9. [ online] [retrieved Jul. 29, 2023]. URL:<https://www.nature.com/articles/ncomms11235> (Year: 2016).*

(Continued)

*Primary Examiner* — Aaron A Priest
*Assistant Examiner* — Randi Lynn Beil
(74) *Attorney, Agent, or Firm* — Goodwin Procter LLP

(57) ABSTRACT

Methods are disclosed for high throughput identification of optimized template-independent polymerase variants. The methods comprise generation of polymerase gene-encoding variants, isolation of variants, expression of variants, exposing expressed polymerase variants to desired conditions for activity, and identification of active variants, such as by hybridization to synthesized polynucleotides or by amplification. Encoding genes of active variants can be sequenced. The method can be performed iteratively to enhance generation and selection of preferred variants.

9 Claims, 6 Drawing Sheets

Specification includes a Sequence Listing.

(56) References Cited

OTHER PUBLICATIONS

Larsen et al. A general strategy for expanding polymerase function by droplet microfluidics, Supplemental Information. Nature Communications. 7, 2016, 1-13. [online] [retrieved Aug. 14, 2023]. URL:<https://www.nature.com/articles/ncomms11235> (Year: 2016 ).*

Ligation-based Library Preparation. Integrated DNA Technologies [online], 2020, [retrieved on Dec. 12, 2024]. Retrieved from the Internet <URL:https://web.archive.org/web/20200220031838/https://www.idtdna.com/pages/technology/next-generation-sequencing/library-preparation/ligation-based-library-prep> (Year: 2020).*

Maga et al. DNA elongation by the human DNA polymerase λ polymerase and terminal transferase activities are differentially coordinated by proliferating cell nuclear antigen and replication protein A. Journal of Biological Chemistry. 280, 2005, 1971-1981 ( Year: 2005).*

Tunel assay. Wikipedia. 3 pages, revision date Feb. 13, 2019 by user "Citation bot". [Retrieved on Nov. 16, 2024]. Retrieved from Internet: <URL:https://en.wikipedia.org/w/index.php?title=TUNEL_assay&oldid=883109229> (Year: 2019).*

Chua et al., Evolving a Thermostable Terminal Deoxynucleotidyl Transferase, ACS Synth. Biol. 2020, 9, 7, 1725-1735, published Jun. 4, 2020, received Feb. 11, 2020.*

Chica et al. CurrOpin Biotechnol. Aug. 2005;16(4):378-84. (Year: 2005).

Singh et al., Curr Protein Pept Sci. 2017, 18, 1-11 (Year: 2017).

Accession F6RGZ5. Jul. 27, 2011 (Year: 2011).

McCombs et al. AAPS J. Mar. 2015; 17(2): 339-351. (Year: 2015).

Bundy et al. Bioconjugate Chem. 2010, 21, 255-263 (Year: 2010).

ISR-WO of PCT/US17/39120, received on Oct. 12, 2017, 9 pages.

EESR of 17816338.2, received on Jun. 5, 2019, 8 pages.

* cited by examiner

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:

```
                         Synthetic polynucleotide

<400> SEQUENCE: 1
tttttttttt tttttttttt                                                   20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 2
aaaaaaaaaa aaaaaa                                                       16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 3
aaaaaaaaaa aaaaaaaa                                                     18
```

DIRECTED EVOLUTION METHOD FOR TEMPLATE-INDEPENDENT POLYMERASES

CROSS-REFERENCE TO RELATED APPLICATIONS

This application claims the benefit of U.S. Provisional Application No. 62/985,744, filed Mar. 5, 2020, the contents of which is incorporated by reference in its entirety.

REFERENCE TO AN ELECTRONIC SEQUENCE LISTING

This application contains a Sequence Listing that has been submitted electronically in ASCII format and is hereby incorporated by reference in its entirety. Said ASCII copy, created on Mar. 14, 2023, is named ABB-002_SL.txt and is 998 bytes in size.

BACKGROUND

The state of the art for enzyme engineering of template-independent polymerases is testing of individual mutants for activity after expression and protein purification. This traditional approach is cumbersome and requires numerous personnel, equipment, and time, even with robotic automation. Generally, multiple iterations of this process are required (e.g., a Design, Build, and Test cycle) to generate mutant polymerases with desired properties. The mutations to be screened are typically selected based on rational mutagenesis through structure guided design and computational methods. Computational methods can struggle to capture key elements of the polymerase function due to poor understanding of structure-function relationships and the biased nature of enzyme crystallization conditions. Furthermore, traditional screening methods require individual purification and testing of each variant.

What is needed therefore, are new high throughput approaches to enable generation and screening of a much broader number of template-independent polymerase variants in an efficient manner, thus allowing rapid and successful identification of template-independent polymerase variants with desired activity under selected conditions and with selected substrates.

SUMMARY OF THE INVENTION

According to some embodiments, provided herein is a method of providing a template-independent polymerase active under preferred conditions, the method comprising: providing a plurality of nucleic acids each comprising a gene encoding a unique template-independent polymerase variant; subdividing the plurality of nucleic acids into isolated compartments, such that a plurality of compartments each comprise a single unique template-independent polymerase variant gene; expressing said genes so that said isolated compartments further comprise said unique template-independent polymerase variant corresponding to said isolated gene; providing conditions within said compartments desirable for nucleic acid extension by a template-independent polymerase variant; and selectively enriching for nucleic acids encoding template-independent polymerase variants active under said conditions.

In some embodiments, the gene is expressed in said isolated compartments.

In some embodiments, the nucleic acids are contained within a host cell capable of expressing said gene. In some embodiments, the gene is expressed in said host cell before subdividing said plurality of nucleic acids into said isolated compartments.

In some embodiments, the method further comprises sequencing the genes encoding template-independent polymerase variants active under said conditions.

In some embodiments, the genes are expressed in vitro in isolation so that each expressed template-independent polymerase variant remains linked to its corresponding gene.

In some embodiments, the enriching step comprises amplifying a template-independent polymerase gene encoding a template-independent polymerase variant active under said conditions. In some embodiments, the enriching step comprises hybridizing a polynucleotide comprising said template-independent polymerase gene encoding a template-independent polymerase variant active under said conditions to a probe.

In some embodiments, the enriching step comprises hybridizing a polynucleotide extended by said template-independent polymerase variant active under said conditions to a probe. In some embodiments, the polynucleotide comprises said template-independent polymerase gene encoding said template-independent polymerase variant active under said conditions. In some embodiments, the polynucleotide is capable of hybridizing to a polynucleotide comprising said template-independent polymerase variant active under said conditions. In some embodiments, the polynucleotide comprising said template-independent polymerase variant active under said conditions is a plasmid.

Also provided herein, according to some embodiments, is a method of selecting a template-independent polymerase active under desired conditions, comprising: providing a plurality of host cells each comprising a plasmid comprising a gene expressing a unique template-independent polymerase variant; subdividing the plurality of host cells into compartments; exposing said compartments to conditions desirable for template-independent polymerase activity; contacting the contents of said host cell in each compartment with reagents to perform nucleic acid extension when said expressed template-independent polymerase variant is active under said conditions, wherein said nucleic acid extension reaction product is coupled with said plasmid encoding said active template-independent polymerase variant in each compartment; pooling said compartments into a mixture; and selectively enriching for nucleic acid extension reaction products coupled with said plasmids encoding said active template-independent polymerase variant from said mixture, thereby selecting plasmids comprising genes encoding template-independent polymerase variants active under said conditions.

In some embodiments, the coupling step comprises synthesis of said nucleic acid extension reaction product at a free 3' end of said plasmid, wherein said plasmid has been cleaved. In some embodiments, the method further comprises cleaving said plasmid.

In some embodiments, the nucleic acid extension is performed on a target oligonucleotide, wherein said target oligonucleotide is capable of binding to said plasmid.

In some embodiments, the plasmid comprises means for binding to said synthesized oligonucleotide.

In some embodiments, the plasmid comprises a target oligonucleotide hybridization region comprising a sequence complementary to a portion of said target oligonucleotide. In some embodiments, the target oligonucleotide hybridization region comprises at least 15, at least 20, or at least 25 nucleotides complementary to said portion of said target oligonucleotide. In some embodiments, the target oligonucleotide hybridization region binds to said target oligonucleotide preferentially over formation of plasmid secondary structure. In some embodiments, the binding of said target oligonucleotide hybridization region and said target oligonucleotide has a melting temperature at least 5° C. greater than plasmid secondary structure binding to said target oligonucleotide hybridization region.

In some embodiments, the target oligonucleotide comprises said plasmid. In some embodiments, the plasmid comprises a cleavage site. In some embodiments, the plasmid is cleaved at said cleavage site to form said 3' end of said target oligonucleotide. In some embodiments, the cleavage site is common to all of said plasmids.

In some embodiments, at least 50%, at least 60%, at least 70%, at least 80%, or at least 90% of the compartments comprise one or fewer host cells.

In some embodiments, the method further comprises sequencing the enriched template-independent polymerase gene variants.

In some embodiments, the template-independent nucleotide addition reaction comprises addition of a plurality of identical nucleotides to said target oligonucleotide to form a homopolymer bound to said target oligonucleotide.

In some embodiments, the template-independent nucleotide addition reaction comprises addition of only one nucleotide to said target oligonucleotide. In some embodiments, the nucleotide comprises a binding moiety. In some embodiments, the nucleotide comprises a reversible terminator. In some embodiments, the method further comprises capping said unreacted target oligonucleotides with a capping group. In some embodiments, the capping group comprises a ddNTP. In some embodiments, the method further comprises removing said reversible terminator after capping said unreacted nucleic acids.

In some embodiments, the conditions comprise the presence of reagents that destabilize the secondary structure formation of DNA. In some embodiments, the conditions comprise a temperature of at least 37° C., at least 42° C., or at least 55° C. In some embodiments, the conditions comprise a modified nucleotide substrate. In some embodiments, the modified nucleotide comprises a nuclease resistant modification. In some embodiments, the modified nucleotide comprises a phosphorothioate modification.

In some embodiments, the conditions comprise a timed reaction to select for kinetic efficiency. In some embodiments, the reaction is terminated by thermal denaturation or addition of EDTA. In some embodiments, the conditions comprise a selected divalent ion cofactor. In some embodiments, the conditions comprise a reaction buffer. In some embodiments, the conditions comprise the presence of polymerase inhibitors. In some embodiments, the conditions comprise the presence of protease or nuclease activity.

In some embodiments, at least some of the template-independent polymerase variants are active under said conditions.

In some embodiments, the reagents comprise a single type of nucleotide so that said template-independent nucleotide addition reaction generates a homopolymer. In some embodiments, the reagents comprise multiple types of nucleotides so that said template-independent nucleotide addition reaction generates a heteropolymer.

In some embodiments, the reagents comprise an endonuclease capable of cleaving said plasmid at said cleavage site. In some embodiments, the reagents comprise a reaction buffer compatible with said endonuclease and said template-independent polymerase. In some embodiments, the plasmid is cleaved in the host cell, such that no endonuclease is needed as part of the emulsion reagents.

In some embodiments, the reagents comprise an enzyme capable of disrupting said host cell. In some embodiments, the enzyme capable of disrupting said host cell wall is a lysozyme.

In some embodiments, the enrichment step comprises an amplification reaction specific for nucleic acids encoding an active template-independent polymerase. In some embodiments, the amplification reaction comprises at least one primer comprising said synthesized oligonucleotide. In some embodiments, the amplification reaction comprises binding of a primer to said synthesized oligonucleotide. In some embodiments, the enrichment step comprises hybridization of said synthesized oligonucleotide to a probe. In some embodiments, the host cell is E. coli or S. cerevisiae.

In some embodiments, the method selects from at least $10^2$, $10^3$, $10^4$, $10^5$, $10^6$, $10^7$, $10^8$, or $10^9$ unique template-independent polymerase variants.

In some embodiments, the method is iterated with the enriched template-independent polymerase variants obtained at each cycle at least 2×, at least 3×, at least 4×, at least 5×, at least 6×, at least 7×, at least 8×, at least 9×, or at least 10× to further optimize template-independent polymerase activity at said desired conditions. In some embodiments, the conditions are modified at each cycle to enhance selection of a template-independent polymerase towards a final set of desired conditions.

In some embodiments, providing said plurality of host cells comprises: providing a plurality of said nucleic acid plasmids each comprising said gene encoding said template-independent polymerase variant; introducing said plurality of nucleic acid plasmids individually into said plurality of host cells; and expressing said genes in said host cells to form template-independent polymerase variants encoded by said genes, wherein each host cell expresses a unique template-independent polymerase variant.

Also provided herein, according to some embodiments, is a library of plasmids each comprising a gene encoding one of a unique template-independent polymerase variant, wherein said plasmid comprises for binding said gene to a synthesized oligonucleotide generated by said template-independent polymerase variant. In some embodiments, the means for binding said gene to said synthesized oligonucleotide comprises a sequence on said plasmid complementary to a portion of said synthesized oligonucleotide. In some embodiments, the means for binding said gene to said synthesized oligonucleotide comprises a cleavage site, wherein said synthesized oligonucleotide is added to the 3' end of said plasmid at said cleavage site.

Also provided herein, according to some embodiments, is a library of host cells each comprising one of said plasmids from the library of plasmids each comprising a gene encoding one of a unique template-independent polymerase variant.

Also provided herein, according to some embodiments, is a plurality of isolated compartments each comprising one of said plasmids from said library library of host cells each comprising one of said plasmids from the library of plasmids each comprising a gene encoding one of a unique template-independent polymerase variant.

In some embodiments, the plurality of isolated compartments each comprise a host cell generated by: providing a plurality of said nucleic acid plasmids each comprising said gene encoding said template-independent polymerase variant; introducing said plurality of nucleic acid plasmids individually into said plurality of host cells; and expressing said genes in said host cells to form template-independent polymerase variants encoded by said genes, wherein each host cell expresses a unique template-independent polymerase variant.

In some embodiments, the plurality of isolated compartments each comprise: an enzyme capable of disrupting the host cell wall to release the contents of said host cell into said compartment, and reagents for performing a template-independent nucleotide addition reaction.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale, emphasis instead placed upon illustrating the principles of various embodiments of the invention.

DETAILED DESCRIPTION

Figure 1:
FIG. 1 illustrates a process of providing a plasmid comprising a gene encoding a template-independent polymerase variant, and generation of a library of diverse variants, e.g., by mutational diversity.

The details of various embodiments of the invention are set forth in the description below. Other features, objects, and advantages of the invention will be apparent from the description and the drawings, and from the claims.

Overview

Provided herein are methods for high-throughput engineering and optimization of template-independent nucleic acid polymerases. These methods readily identify mutations that improve desirable properties of template-independent polymerases and to create combinatorial versions of the mutations to generate improved enzyme variants.

According to some embodiments, the screening method described herein enables orders of magnitude more mutants be tested compared to traditional methods. Further, the screening methods described herein can be performed without requiring protein purification, and the iteration of the process can be performed without an intervening step to check the activity of mutant polymerases. The invention can be used to improve the properties of polymerases with template-independent activity or to introduce template-independent activity to a templated polymerase. Here, the invention is utilized to improve desirable properties of an exemplary template independent polymerase Terminal deoxynucleotidyl Transferase (TdT). The invention allows for the simultaneous testing of billions of mutant TdT variants, and the subsequent enrichment of desired variants through either capture-based or PCR based-enrichment. Altering of conditions allows for enrichment of TdT polymerases with desirable properties (e.g. thermostability, kinetic efficiency, utilization of non-standard nucleotide substrates, tolerance towards certain chemicals such as denaturants, utilization of other divalent ions as cofactors, etc.).

The invention enables screening of billions of template-independent polymerase variants, while conventional methods are limited to a few thousand polymerases. The advantage over existing solutions is that the screening of larger libraries strongly accelerates and simplifies the identification of new desirable enzyme variants, and further enables the generation of novel enzyme variants that would not be found with small library sizes. Furthermore, the disclosed process is much cheaper and less labor-intensive.

The invention solves the limitations of conventional screening for template-independent polymerases by enabling a high-throughput screen that does not require individual purification and testing of each variant. Instead, template-independent polymerase variants are tested for their activity in droplets, and a link of the activity to the gene sequence is generated that enables enrichment of polymerase-variants with desired activity.

Improved Template-Independent Polymerases

The invention describes a method for the high-throughput evolution of template-independent polymerases. Performing the method a single time allows for the simultaneous testing of billions of mutant polymerases (i.e. a gene "Library") in a rapid amount of time. The method can be modified in myriad ways to allow for the enrichment and capture of polymerases with desired properties (e.g. increased thermostability, improved kinetics, or utilization of non-standard substrates). The method can be iterated multiple times to continuously enrich for mutants with desired properties without the need to test individual polymerases for function.

In one aspect, the invention is directed to a method for providing a template-independent polymerase active under preferred conditions comprising the steps of:
- a) providing a plurality of nucleic acids each comprising a gene encoding a unique template-independent polymerase variant;
- b) subdividing the plurality of nucleic acids into isolated compartments, such that a plurality of compartments each comprise a single unique template-independent polymerase variant gene;
- c) expressing said genes so that said isolated compartments further comprise said unique template-independent polymerase variant corresponding to said isolated gene;
- d) providing conditions within said compartments desirable for nucleic acid extension by a template-independent polymerase variant; and
- e) selectively enriching for nucleic acids encoding template-independent polymerase variants active under said conditions.

In addition, in some embodiments, the invention is directed to a method for providing a template-independent polymerase active under preferred conditions comprising the steps of:
- a) providing a plurality of host cells each comprising a plasmid comprising a gene expressing a unique template-independent polymerase variant;
- b) subdividing the plurality of host cells into compartments;
- c) exposing said compartments to conditions desirable for template-independent polymerase activity;
- d) contacting the contents of said host cell in each compartment with reagents to perform nucleic acid extension when said expressed template-independent polymerase variant is active under said conditions, wherein said nucleic acid extension reaction product is coupled with said plasmid encoding said active template-independent polymerase variant in each compartment;
- e) pooling said compartments into a mixture; and
- f) selectively enriching for nucleic acid extension reaction products coupled with said plasmids encoding said active template-independent polymerase variant from said mixture, thereby selecting plasmids comprising genes encoding template-independent polymerase variants active under said conditions.

Template-Independent Polymerase Library

In some embodiments, the method includes the step of providing a plurality of nucleic acids each comprising a gene encoding a unique template-independent polymerase (TIP) variant. A gene encoding a polymerase enzyme and a library of variants of the gene can be generated using standard techniques for gene "library" generation. For instance, error-prone PCR, site-saturation mutagenesis, gene shuffling, or scanning mutagenesis can be used to introduce mutations into the polymerase encoding gene (FIG. 1). These genes can be inserted into a vector. In some embodiments, polymerases or template-independent enzymes are encoded on a plasmid (e.g. a pET Vector (Novagen).

Compartmentalization and Expression

In some embodiments, the method includes the step of subdividing the plurality of nucleic acids into isolated compartments, such that a plurality of compartments each comprise a single unique template-independent polymerase variant gene. In some embodiments, the method includes the step of expressing the TIP variant genes so that the isolated compartments further comprise the unique template-independent polymerase variant corresponding to the gene variant. Thus, after separation of genes encoding TIP variants into compartments, the gene is then expressed so that an expressed TIP variant protein is contained within each compartment. This can include transcription and translation of the encoding genes in vitro after encapsulation, so that the in vitro expressed variants are separated into compartments.

Figure 2A:
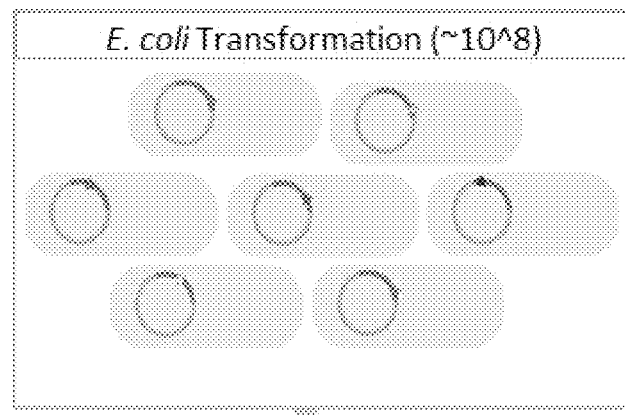
FIG. 2 illustrates an embodiment of compartmentalizing expressed variants and reaction components in a droplet, according to an embodiment of the invention. As shown, (A) transformed host cells comprising plasmids from the template-independent polymerase variant gene library are provided, (B) expression of the polymerase variants is induced within each transformed host cell, and (C) each host cell is compartmentalized within a droplet with reagents for disrupting the host cell wall to release the plasmid and polymerase variants into the droplets (lysozyme) cleaving the plasmid to generate a free 3' end (endonuclease) and substrate for polymerase addition of a homopolymer to the free 3' end (dATP). Also shown is a buffer compatible with each enzyme in the droplet.
Figure 2B:
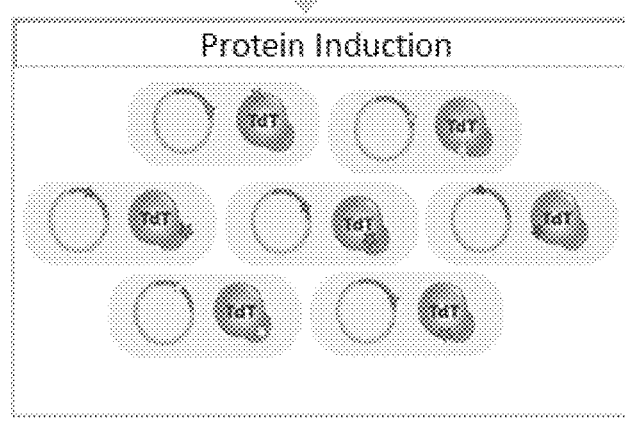
Figure 2C:
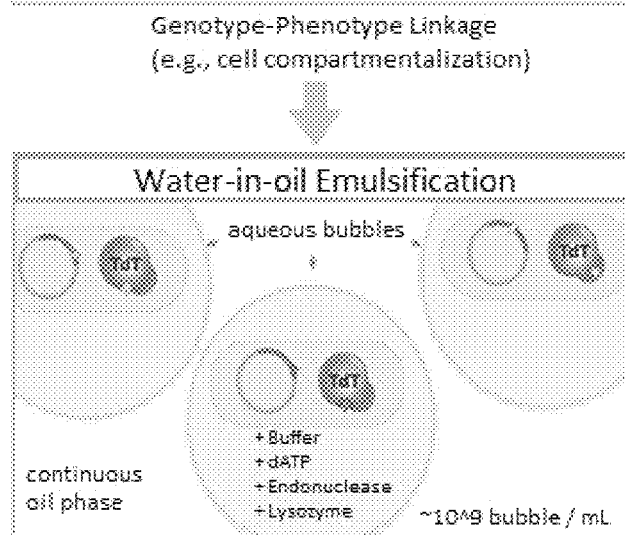

In a preferred embodiment, the TIP variant library is transformed into a suitable microbial host useful for gene expression (e.g. *E. coli* or *S. cerevisiae*) (FIG. 2, part A)). The microbial host expresses the library of polymerases through standard expression systems (e.g. IPTG, Galactose, etc.). The microbial host acts as a physical barrier to encapsulate individual library members and their corresponding mutant polymerase (a so-called genotype-phenotype linkage), in addition to expression of the mutant proteins (FIG. 2, part B). In some embodiments, the TIP variant genes are encoded on a plasmid, and the plasmid is inserted into the host cell, such as *E. coli*, for expression of the template-independent polymerase variant within each transformed host cell. In some embodiments, at least 50%, at least 60%, at least 70%, at least 80%, or at least 90% of the compartments comprise one or fewer host cells.

For variant genes expressed within a host cell system, the expressed TIP variants must be released from the host cell in order to perform the selection assay. However, so that the selection assay is specific to the expressed variant, the released contents of the host cell must remain isolated from that of other host cells. Therefore, in some embodiments, the method includes encapsulating individual transformed host cells within droplets.

In some embodiments, individual transformed host cells are isolated within droplets by placing the host cells into a water-in-oil emulsion with a suitable aqueous solution (FIG. 2, part C). In some embodiments, the aqueous solution comprises a lysozyme or other enzyme to promote degradation of the cell wall to expose the expressed TIP variants within the cell to the aqueous solution and polymerase assay reagents.

In some embodiments, the aqueous solution comprises nucleoside triphosphates which are used by an active TIP variant to form a polynucleotide. In some embodiments, the aqueous solution comprises a pH controlled buffer or metal-ions to optimize conditions for template-independent polymerase activity and selection. In some embodiments, the aqueous solution comprises an enzyme for cutting the plasmid encoding the library of polymerases (e.g. a restriction enzyme).

The water-in-oil emulsion is a stable entity that physically separates cells and reaction components that will not cross-talk with other compartments throughout the process. The compartments serve to separate mutant plasmids, as well as their corresponding mutant polymerase and additional reaction components.

Template-Independent Polymerase Variant Activity

In some embodiments, the method includes providing conditions within the compartments holding isolated expressed TIP variants desirable for nucleic acid extension by the TIP variants. Within the compartment is a polynucleotide comprising a free 3' end which serves as a starting point for template-independent polymerase. This polynucleotide is or can be physically linked to the gene encoding the TIP variant in each compartment. In this way, the template-independent polymerase variant reaction product is physically linked to the gene encoding the variant, and can be used to identify which TIP variant genes encode active polymerases under the desired conditions.

In some embodiments, the template-independent nucleotide addition reaction comprises addition of a plurality of identical nucleotides to the free 3' end of the polynucleotide to form a homopolymer bound to the 3' end. Thus, in some embodiments, template-independent nucleotide addition reaction comprises addition of only one nucleotide to the 3' end of the polynucleotide (e.g., the cleaved plasmid or the target oligonucleotide). In some embodiments, the compartment comprises a nucleotide comprising a binding moiety, and a TIP variant catalyzes addition of a nucleotide comprising a binding moiety. This binding moiety can then be used to specifically capture a polynucleotide bound to the binding moiety (indicating TIP polymerase variant activity). In some embodiments, the compartment comprises a nucleotide comprising a reversible terminating moiety (i.e., a reversible terminator), and a TIP variant catalyzes addition of a reversible terminator to the 3' end of the polynucleotide.

In some embodiments, a capping reaction can be performed to an unreacted free 3' end of the polynucleotide to inhibit further addition. For example, after completion of addition of a reversible terminator, unreacted free 3' ends may be capped, followed by a step to remove the reversible terminating moiety from the added nucleotides, thereby facilitating addition of another group that allows binding and enrichment (e.g., a homopolymer or polynucleotide comprising a binding moiety) at the end of only uncapped polynucleotides. In some embodiments, the capping group comprises ddNTP.

As described herein, the screening method to identify active TIP variants can be used to develop TIP variants active under selected or preferred conditions. In some embodiments, the preferred conditions include a temperature of at least 37° C., at least 42° C., or at least 55° C. In some embodiments, preferred conditions include incorporation of a modified nucleotide substrate into the polynucleotide, such as a nucleotide comprising a nuclease resistant modification, a phosphorothioate modification, or a reversible termination moiety. In some embodiments, the TIP variants are screened for reaction speed or increased activity. In some embodiments, the preferred conditions include a selected divalent ion or cofactor. In some embodiments, the preferred conditions include a desired reaction buffer. In some embodiments, the preferred conditions include resistance to polymerase inhibitors, protease activity, or nuclease activity.

3' End-Plasmid Cleavage

In some embodiments, the free 3' end is generated by cutting a plasmid containing the TIP variant gene. In this manner, a polymerase extension reaction will occur directly on the polynucleotide encoding the TIP variant if the variant is active under the desired conditions.

Therefore, in some embodiments, the plasmid encoding the TIP variant comprises a DNA sequence that encodes for a site to be cleaved. Suitable cleavage sites include, e.g., a restriction enzyme recognition site, a homing endonuclease site, or a CRISPR guide RNA site. Any labile site recognized by an enzyme or chemical known to one of skill in the art can be used.

In some embodiments, the restriction enzyme cuts the plasmid one or multiple times. In preferred embodiments, the cleavage site is located outside the coding region of the polymerase gene under selection. In preferred embodiments, the cleavage enzyme is co-expressed in the same compartment or host cell as the TIP variant. In some embodiments, the plasmid comprises both a gene encoding the TIP variant and a gene encoding the cleavage enzyme. In preferred embodiments, the co-expressed cleavage enzyme cleaves one strand of the DNA sequence. In preferred embodiments, a buffer is used that is compatible with both the cleavage enzyme (e.g., a restriction enzyme) and the polymerase, allowing both to operate simultaneously or sequentially. As described herein, the cleavage of the plasmid serves to create 3' ends on the plasmid from which the template-independent polymerase may act to synthesize a homo-polymer.

3' End Separate Target Oligonucleotide

Figure 3:
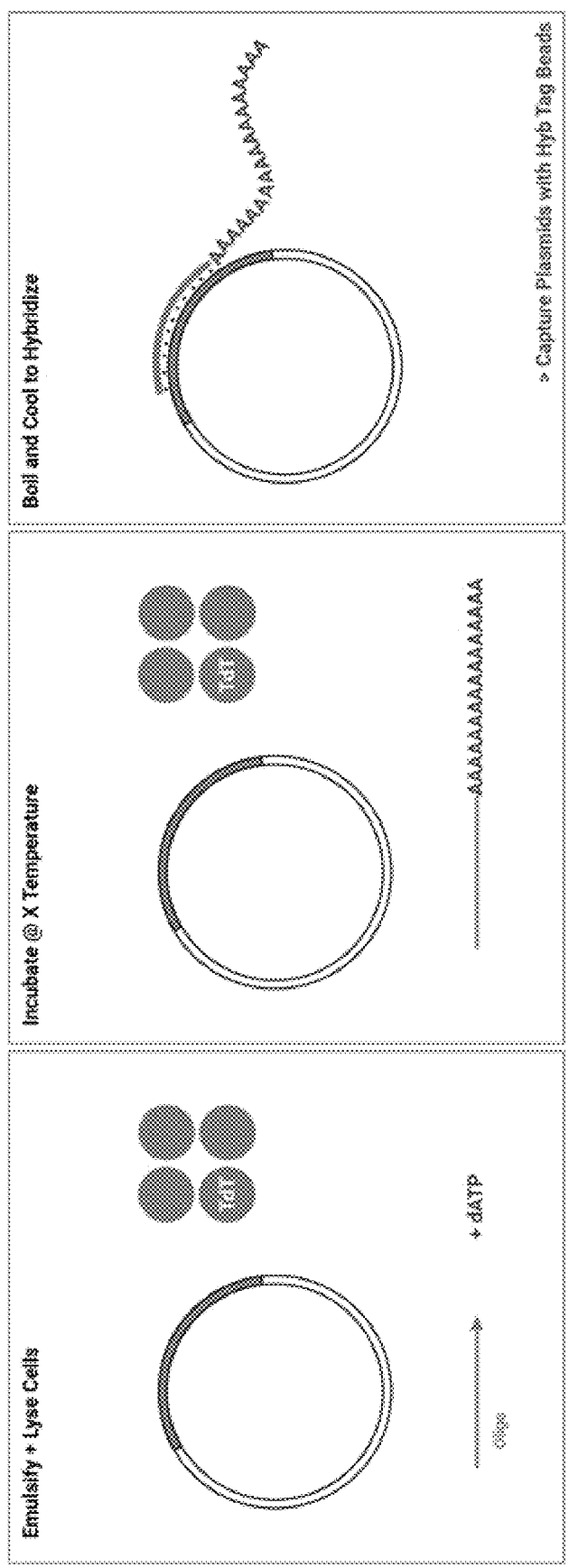
FIG. 3 illustrates an embodiment where the TIP variants (TdT) form a poly A tail on a free 3' end of a polynucleotide (i.e., target oligonucleotide) separate from the plasmid encoding the polymerase variant, where the polynucleotide comprises a region configured to hybridize specifically to the plasmid, according to an embodiment of the invention. Nucleic acid sequences corresponding to SEQ ID NOs.: 2 and 3 are shown in the middle and right-most panel, respectively.

In some embodiments, the free 3' end is on a polynucleotide (i.e., a target oligonucleotide) comprising a sequence complementary to a region of the polynucleotide which encodes the TIP variant (FIG. 3). This separate polynucleotide is included in the isolated compartment as part of the reaction components for the TIP variant. In this manner, a polymerase extension reaction will occur on a polynucleotide that can hybridize specifically to the polynucleotide encoding the TIP variant or a polynucleotide attached to the TIP variant gene, and therefore be physically linked. In some embodiments, the template-independent polymerase extends a short nucleic acid molecule within the compartment into a homo-polymer primer that could then be used to selectively amplify a TIP variant gene within the compartment. In some embodiments, the polynucleotide comprising the free 3' end comprises modified nucleotides to inhibit degradation.

In a preferred embodiment, the binding affinity between the target oligonucleotide and the polynucleotide comprising the gene encoding the TIP variant is high enough to allow stable bond formation for capture of the complex from a pooled solution of polynucleotides. For example, when the polynucleotide comprising the TIP variant gene is a plasmid and the oligonucleotide binds to the plasmid via hybridization of a complementary sequence, the stability of the interaction between the target oligonucleotide and the plasmid must be much higher than the self-interaction of other regions of the plasmid with the target oligonucleotide binding region. In some embodiments, the hybridization of complementary base pairs between the target oligonucleotide and the plasmid allows the target oligonucleotide to serve as a primer for a subsequent downstream amplification of the TIP variant gene.

Overall, an important aspect of the invention is to provide within each compartment a polynucleotide comprising a free 3' end that can act as a starting point for oligonucleotide synthesis by an active TIP variant, wherein the polynucleotide also is bound or is capable of being bound to the gene encoding the TIP variant. Thus, in some embodiments, the polynucleotide comprising the gene encoding the TIP variant comprises or is bound to a target oligonucleotide hybridization region comprising a sequence complementary to a portion of the target oligonucleotide. In some embodiments, the target oligonucleotide hybridization region comprises at least 15, at least 20, or at least 25 nucleotides complementary to said portion of said target oligonucleotide. In order to facilitate preferential binding, in some embodiments the target oligonucleotide hybridization region binds to said target oligonucleotide preferentially over formation of secondary structure within the polynucleotide. In some embodiments, binding of said target oligonucleotide hybridization region and said target oligonucleotide has a melting temperature at least 5° C. greater than plasmid secondary structure binding to said target oligonucleotide hybridization region.

Substrates

For the polymerase reaction, the template independent polymerase may utilize the nucleotide triphosphates added to the compartment. In preferred embodiments, a single nucleoside triphosphate will be added to the reaction so that an active TIP variant will synthesize a homopolymeric polynucleotide chain at the free 3' end. For example, a dATP nucleotide substrate will create a poly-A tail whose presence and/or size is dependent on the activity of the co-encapsulated polymerase variant. In some embodiments, the single nucleotide added to the reaction is dATP, dGTP, dCTP, or dTTP. In some embodiments, instead of single nucleotide triphosphates, di/- or polynucleotides with a 5' triphosphate could be used in the selection mechanism.

In some embodiments, the above screening process can be used to generate optimized TIP polymerase variants incorporating 3' reversible termination groups, in which case only one extension would occur. Following that single extension, all unextended molecules could be irreversibly blocked, e.g., based on ddNTP, followed by unblocking of the reversible terminator, which will selectively make the ends that received RTdNTPs available for downstream processing, e.g. by tailing, and therefore for selection.

In such embodiments where the host cells are lysed, a cell is likely to release nucleases that can degrade DNA, such as a homopolymer generated by active TIP variants. Thus, in some embodiments, nucleotides included in the compartment and added to the free 3' end of the polynucleotide may include a number of modifications to enhance the process, such as an alpha-phosphorothioate moiety which can block endogenous exonuclease activity present in the host cell and stabilize the extended polynucleotide reaction product. Furthermore, after a thermostable template-independent polymerase is developed using the method described herein, the reaction can include use of heat to inactivate such nucleases when thermostable variants are used.

Reaction Initiation and Termination

The reaction is then stopped after a preferred time so that the reaction products can be combined without cross-contaminating polymerase activity. The reaction can be stopped, e.g., by thermal denaturation or addition of EDTA. Once the reaction is stopped, the contents of the isolated compartments can be combined into a single aqueous volume. In some embodiments, combining the isolated compartments comprises breaking the emulsion droplets containing each isolated polymerase variant, encoding gene, and reaction product if the variant is active.

In some embodiments, photolabile nucleotides, e.g. with a 3'-O-Nitrobenzyl modification, could be used to enable selective activation of the extension reaction in the droplets by irradiation with visible or UV light.

Enrichment of Genes Encoding Active TIP Variants

In some embodiments, the method comprises the step of selectively enriching for nucleic acids encoding template-independent polymerase variants active under the desired conditions. In some embodiments, the enriched nucleic acid population comprising genes encoding active template-independent polymerase variants is sequenced to identify the enriched gene sequences.

In some embodiments, the homopolymeric tail created by active polymerases may be selectively enriched by a variety of methods including PCR or capture with a hybridization probe. This step enriches polymerases which were capable of synthesizing a compatible tail. Following the post-emulsion enrichment, polymerase sequences can be analyzed through methods such as DNA sequencing or can be further processed and re-cloned to iterate the process and achieve further enrichment.

Instead of selective amplification of genes that have been extended with a DNA tail, pull-down of those genes can be performed based on hybridization of the created tail to a complementary DNA sequence. Further, in some embodiments, enrichment of genes encoding active TIP variants can be performed by binding to a binding moiety on a modified nucleotide by the TIP variant.

In some embodiments, nucleotides or dinucleotides with 3' modifications can be used for subsequent ligation (e.g. chemical ligation to an azide) to select for extended strands. This enables higher specificity and reduced background amplification.

Cycled Selection

In some embodiments, the method described herein can be iterated with the enriched template-independent polymerase variants obtained in each cycle to further optimize template-independent polymerase activity at the desired conditions. Such a process can be iterated several times, including at least 2×, at least 3×, at least 4×, at least 5×, at least 6×, at least 7×, at least 8×, at least 9×, or at least 10×. In addition, conditions can be modified at each cycle to enhance selection of a TIP variant towards an activity under desired conditions. For example, the temperature that the reaction is performed at can be increased at each cycle. Sequencing of each variant is not necessary at each iteration. However, additional variants can be created based on the enriched variants at each cycle by introducing further mutational diversity based on the variants, e.g., by error-prone PCR, site saturation mutagenesis, gene shuffling, and scanning mutagenesis.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1—Generating and Selecting Mutant Polymerases with Improved Activity

Electrocompetent *E. coli* cells were prepared from a culture of BL21GOLD (DE3) cells (Agilent) using standard techniques. Briefly, a stationary culture of BL21GOLD (DE3) cells were seeded into a fresh culture of 2×YT media at a dilution ratio of 1:20 and grown for 1.5 hours shaking at 37° C. Cells were plunged into wet-ice and incubated for 10 minutes. Cells were subsequently centrifuged at 2,000×g for 10 minutes and the supernatant was discarded. Cells were resuspended in 0.5× the initial culture volume of ice-cold sterile H2O. Cells were pelleted following the above procedure for a total of 3 wash steps.

Following washes, the cells were mixed with the DNA containing the library of mutant polymerase plasmids. Standard electroporation protocols were used (for instance using a GenePulser unit (BioRad)). Typically, the process will yield a transformation efficiency of at least 10 million colony forming units. The transformed cells were grown overnight in 2×YT with an appropriate antibiotic to selectively grow cells that received a plasmid containing a mutant polymerase.

Transformed cells were processed to allow for the induction of mutant polymerases. Overnight cultures of transformed cells were seeded at a dilution ratio of 1:60 into 2×YT with appropriate antibiotic and grown shaking at 37° C. Cells were grown to an optical density at 600 nm to ~0.3-0.5 units. Cells were then incubated at room temperature for 45 minutes followed by an additional incubation at 12° C. for 45 minutes. Cells were then induced with IPTG to a final concentration of 0.5 mM and grown overnight (~16 hours) at 12° C.

The following day, induced cells were then prepared to be emulsified. 200 microliters of cells were centrifuged at 3,000×g for 5 minutes. Cells were washed in 150 microliters of 1× Cutsmart buffer (NEB). Cells were again centrifuged at 3,000×g for 5 minutes.

Cells were resuspended in 150 microliters of the selection buffer containing (1× Cutsmart buffer, 250) micromolar Cobalt Chloride, 333 micromolar 2'-Deoxyadenosine-5'-O-(1-Thiotriphosphate), 0.3 micrograms of Hen Egg Lysozyme, and 15 units of I-CeuI (NEB)).

Cells were then added to the oil mix containing: 438 microliters Tegosoft (DEC) (Evonik), 42 microliters ABIL-WE09 (Evonik), 120 microliters of mineral oil (Sigma), and a 1 milliliter syringe plunger. The cell and oil mix was then placed on a TissueLyser (Qiagen) and shaken at 42 Hz for 4 minutes. The emulsion mixture was then incubated at −80° C. for 10 minutes to freeze solid. The mixture is then incubated at a given selective temperature and time period to test for template-independent polymerase activity.

Following the reaction, emulsions were broken by spinning the reaction for 5 minutes at 10,000×g and removing the oil phase, adding 150 microliters of 25 millimolar EDTA and 750 microliters of chloroform with vortexing. The aqueous fraction was then collected and purified using a standard PCR cleanup kit (e.g. Monarch cleanup kit (NEB)).

The resulting DNA containing the linearized plasmid and extended 3' tail were then enriched utilizing a downstream PCR reaction with a complementary homopolymeric primer and a gene specific primer which will anneal to the plasmid. Alternatively, one may capture homopolymeric tails using a capture probe complementary to the extended 3' tail.

One of skill in the art will recognize that parameters of this protocol can be altered to selectively enrich polymerase variants which are especially suited to function in the given set of parameters.

Multiple rounds of enrichment for increased thermostability as described above were performed. Consistent increase of the performance of the pool as well as mutants with increased thermostability were found as described in Examples 2-4.

Example 2—Activity Measurement Using the Enrichment Method on Control Constructs Encoding Polymerases of Various Activities Testing for polymerase activity of selected variants under selected conditions as described in Example 1 was performed on i) a gene encoding a murine TdT polymerase (lacking the N-terminal BRCT domain and several solvent exposed cysteines), ii) a computationally thermostabilized mutant murine TdT polymerase (BTC), iii) a non-functional truncated murine TdT (XXv2), and iv) a non-functional truncated murine TdT with added bovine TdT (bTdT, New England Biolabs). *E. coli* cells were transformed with plasmids encoding these genes and isolated in an emulsion with components for linearizing and extending the plasmid encoding the TdT variants as described above in Example 1. Constructs were incubated in the emulsion at 37° C. or 45° C. for 2 hours. Following incubation, DNA reaction product was subjected to PCR enrichment using a gene specific 5' primer and a homopolymeric oligo dT (20) (SEQ ID NO.: 1).

Figure 4:
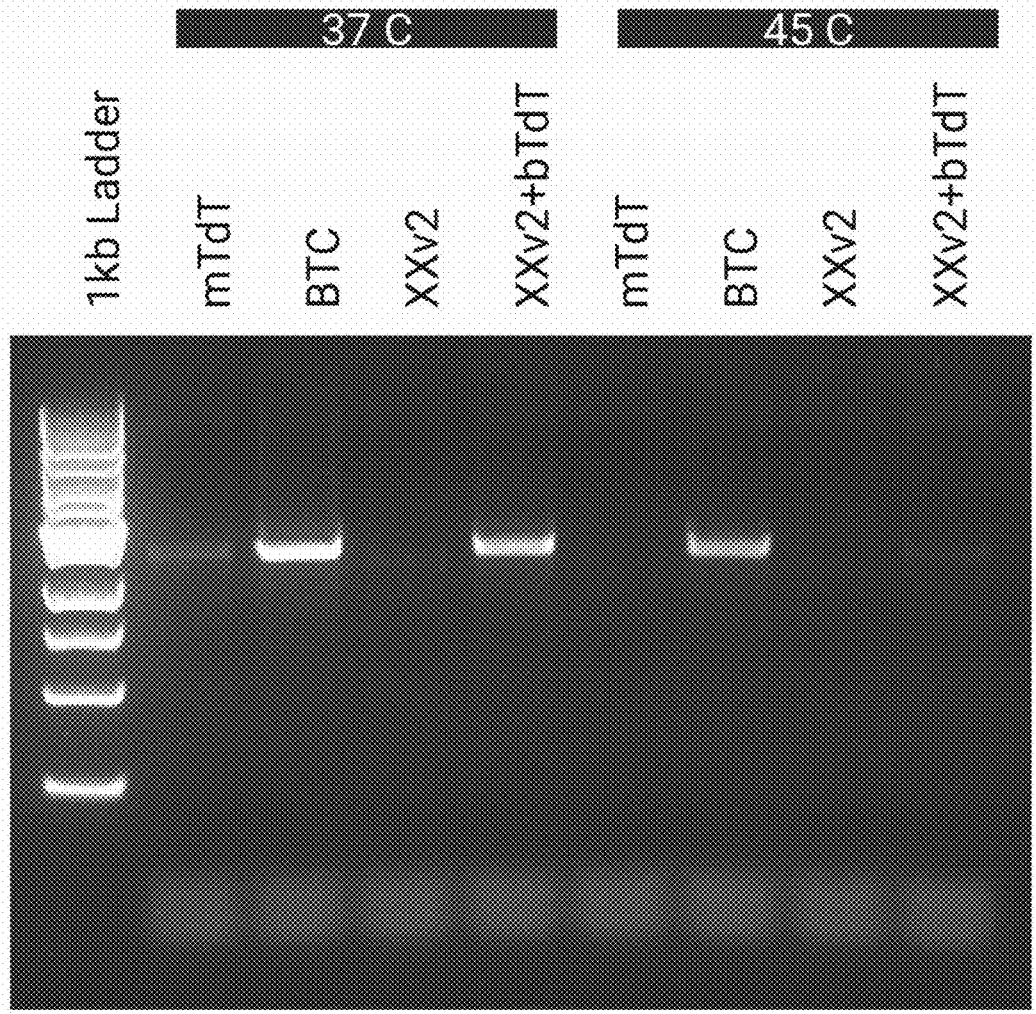
FIG. 4 shows the results of an amplification of active and inactive polymerase variants after going through the screening process described herein at 37° C. and 45° C. At 45° C., only the mutant with increased thermostability (BTC) maintains its activity and results in a well detectable band. In contrast, the mutant with low thermostability (MTdT) and the inactive mutant after the addition of TdT with low thermostability (XXv2+btdt) show amplification only at 37° C. The inactive variant (XXv2) does not show any activity.

The results are shown in FIG. 4. The appearance of the amplification band is dependent on TdT-activity; At 37° C., the regular mutant, BTC and the positive control with added bovine TdT extend their respective gene and produce an amplification band in the PCR with the poly-dT primer. At 45° C., only the mutant with increased thermostability maintains its activity and results in a well detectable band, thereby allowing for selective enrichment of the more thermostable TdT variant.

Figure 5:
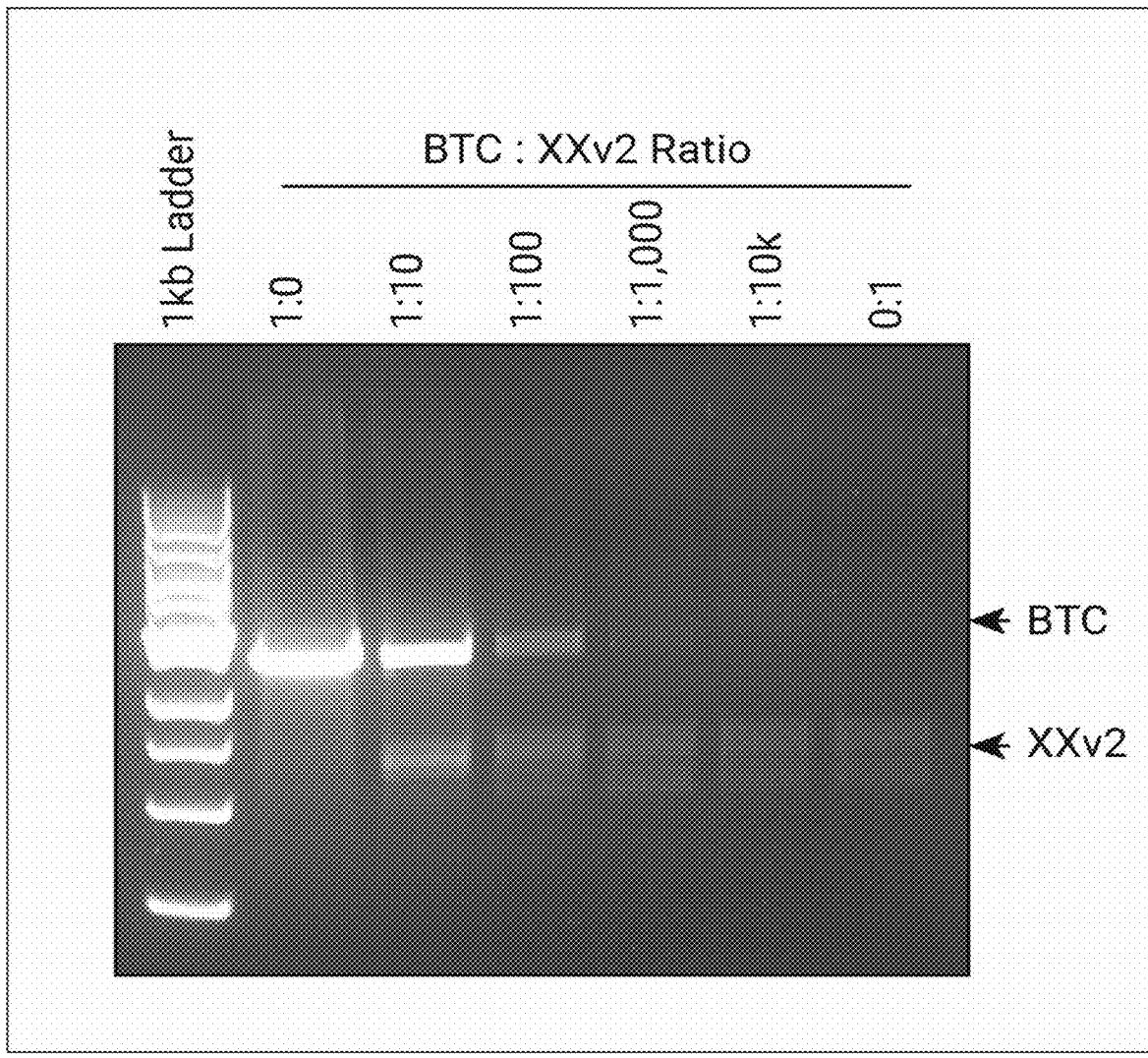
FIG. 5 shows the fold enrichment of active (BTC) to inactive (XXv2) with starting ratios shown on the x-axis, and resulting products from screening shown in the gel. There is about a 100-fold enrichment of the active variant during the selection process.

Example 3—Specific Enrichment of Active Polymerases when Mixed with Excess Inactive Polymerase To test the specific enrichment for active polymerases when performing a single iteration of the method described in Example 1, we mixed a known active TdT mutant, BTC, with an excess of a known inactive TdT mutant (XXv2). The XXv2 plasmid contains a TdT with stop codons in the polymerase open reading frame that creates a truncated polymerase and additionally has a HindIII sequence which can be used as a unique identifier. If no enrichment has occurred, then the starting ratio of active vs. inactive TdT variant would remain constant. If enrichment of active polymerases have occurred then the resulting ratio should shift in favor of the active polymerase. The "fold-enrichment" can be described as a constant that relates the starting ratio of active vs. inactive to the resulting ratio. Several ratios were used to accurately determine the fold-enrichment, including: 1 active to 10 inactive, 1 active to 100 inactive, 1 active to 1,000 inactive, 1 active to 10,000 inactive. The results are shown in FIG. 5. The resulting ratios are estimated as roughly: 10 active to 1 inactive, 1 active to 1 inactive, 1 active to 10 inactive, and 1 active to 100 inactive, respectively, as shown in Table 1 below.

TABLE 1

| Enrichment of active BTC from BTC/XXv2 (inactive) mixture | | |
|---|---|---|
| BTC:XXv2 - Starting Ratio | BTC:XXv2 - Ratio after one round of selection | Fold Enrichment |
| 1:10 | ~10:1 | ~100 |
| 1:100 | ~1:1 | ~100 |
| 1:1,000 | ~1:10 | ~100 |
| 1:10,000 | ~1:100 | ~100 |

This indicates that a roughly 100-fold enrichment of the active polymerase variant has occurred after a single iteration of the process across a wide range of starting ratios. Therefore, our selection methods disclosed herein is capable of significantly enriching for polymerases active under desired conditions across a wide range of starting concentrations.

Example 4—Enrichment of Thermostabilizing Mutations

Figure 6:
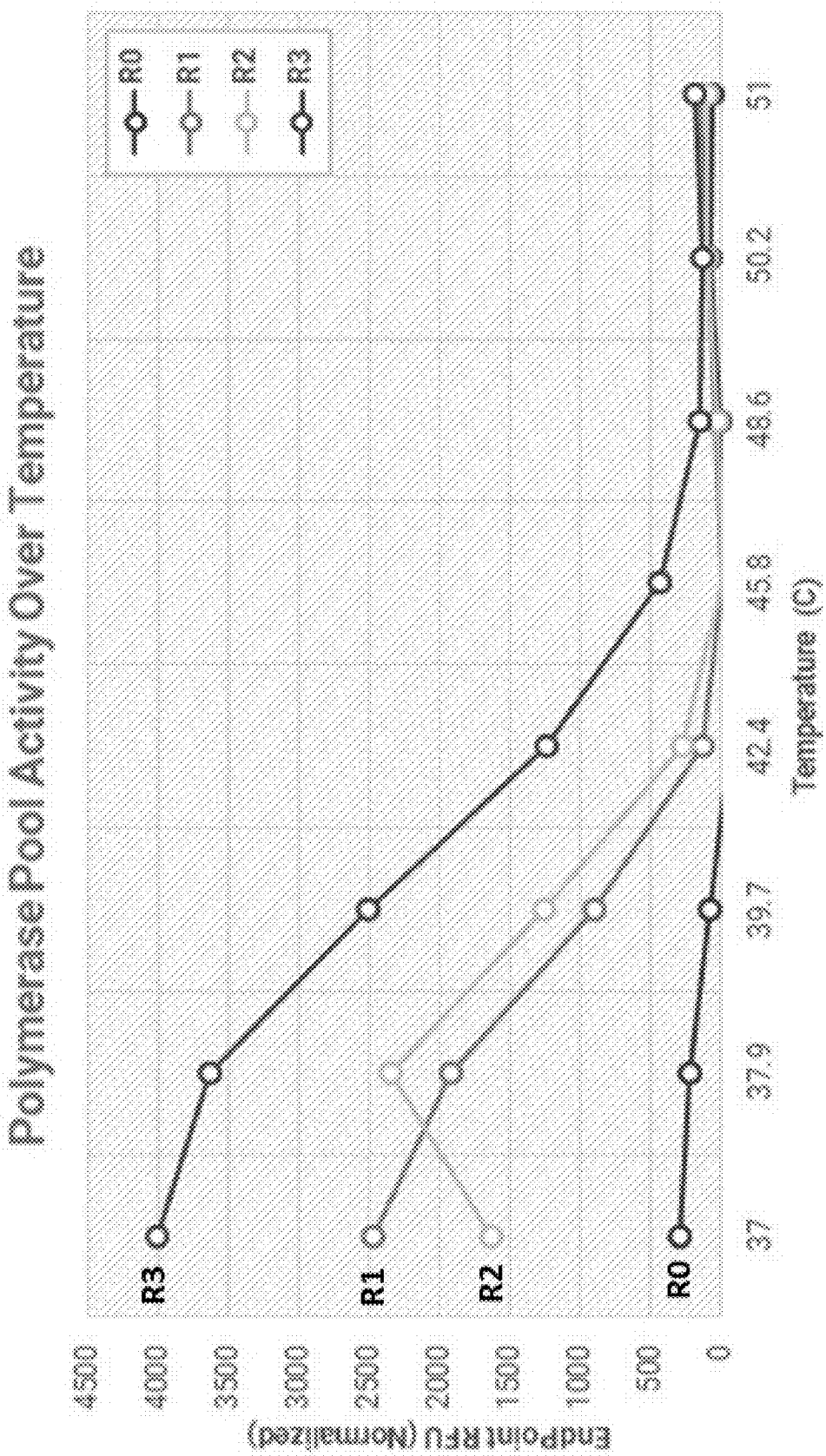
FIG. 6 shows the resulting activity in pools of polymerases after each iterative round of screening. R0 indicates the initial activity of the pool at different temperatures. R1 indicates activity of the pool after a first screen at 37° C. R2 indicates activity of the pool after a second screen at 42° C. R3 indicates activity of the pool after a third screen at 55° C.

To demonstrate that our method can enrich for desired mutations over multiple iterations, a library of mutant TdT polymerases was constructed and the method as described in Example 1 was iterated multiple times with increasing temperatures during the extension reaction. Increasing the temperature enriches for polymerases that can create the homopolymeric tail at the elevated temperature (i.e., thermostable TdT polymerases). The method was iterated for three rounds with increasing temperature and then the resulting pool of polymerase mutants was tested for thermostability. Round 1 (R1) was performed at 37° C., round 2 (R2) at 42° C., and round 3 (R3) at 55° C. The results are shown in FIG. 6. R0 indicates the initial activity of the pool before enrichment. Each successive round of the process (R1, R2, and R3) increased the thermostability in the pool of polymerases. Iteration of the process over multiple cycles and modulation of conditions were successfully used to enrich for the desired activity, with polymerases resulting from R3 having the highest activity at increased temperatures.

Therefore, our selection methods disclosed herein are capable of selectively enriching for polymerase variants having activity under desired conditions, including temperature.

Example 5—Generating and Selecting Mutant Polymerases with Improved Activity with Co-Expression of Polymerase Variants and Endonuclease Enzyme In some cases, conditions desirable for selection of polymerase variants are not compatible with conditions required for the compartmentalized endonuclease to cut the plasmid encoding the polymerase variant to expose the 3' end. To conform the method performed in Example 1 to this situation, we simultaneously expressed the endonuclease with the polymerase variant in the host cell. The endonuclease cut the plasmid, so that the plasmid DNA is already cut prior to emulsification, so that the reaction conditions for the polymerase variant in the emulsification no longer need to be compatible with the cleaving enzyme.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method of selecting a template-independent polymerase active under desired conditions, comprising:
   providing a plurality of host cells each comprising a plasmid comprising a gene expressing a unique template-independent polymerase variant;
   subdividing the plurality of host cells into compartments;
   exposing said compartments to conditions desirable for template-independent polymerase activity;
   contacting the contents of said host cell in each compartment with reagents to generate a nucleic acid extension product when said expressed template-independent polymerase variant is active under said conditions, wherein said nucleic acid extension reaction product is coupled with said plasmid encoding said active template-independent polymerase variant in each compartment, and wherein said coupling comprises synthesis of said nucleic acid extension reaction product at a free 3' end of said plasmid, wherein said plasmid has been cleaved;
   pooling said compartments into a mixture; and
   selectively enriching for nucleic acid extension reaction products coupled with said plasmids encoding said active template-independent polymerase variant from said mixture, thereby selecting plasmids comprising genes encoding template-independent polymerase variants active under said conditions.

2. The method of claim 1, wherein at least 50%, at least 60%, at least 70%, at least 80%, or at least 90% of the compartments comprise one or fewer host cells.

3. The method of claim 1, further comprising sequencing the enriched template-independent polymerase gene variants.

4. The method of claim 1, wherein providing said plurality of host cells comprises:
   providing a plurality of said nucleic acid plasmids each comprising said gene encoding said template-independent polymerase variant;
   introducing said plurality of nucleic acid plasmids individually into said plurality of host cells; and
   expressing said genes in said host cells to form template-independent polymerase variants encoded by said genes, wherein each host cell expresses a unique template-independent polymerase variant.

5. A method of selecting a template-independent polymerase active under desired conditions, comprising:
   providing a plurality of host cells each comprising a plasmid comprising a gene expressing a unique template-independent polymerase variant;
   subdividing the plurality of host cells into compartments;
   exposing said compartments to conditions desirable for template-independent polymerase activity;
   contacting the contents of said host cell in each compartment with reagents to generate a nucleic acid extension product when said expressed template-independent polymerase variant is active under said conditions, wherein said nucleic acid extension is performed on a target oligonucleotide, wherein said target oligonucleotide is capable of binding to said plasmid, and wherein said nucleic acid extension product is coupled with said plasmid encoding said active template-independent polymerase variant in each compartment;
   pooling said compartments into a mixture; and
   selectively enriching for nucleic acid extension reaction products coupled with said plasmids encoding said active template-independent polymerase variant from said mixture, thereby selecting plasmids comprising genes encoding template-independent polymerase variants active under said conditions.

6. The method of claim 5, wherein at least 50%, at least 60%, at least 70%, at least 80%, or at least 90% of the compartments comprise one or fewer host cells.

7. The method of claim 5, further comprising sequencing the enriched template-independent polymerase gene variants.

8. The method of claim 5, wherein providing said plurality of host cells comprises:
- providing a plurality of said nucleic acid plasmids each comprising said gene encoding said template-independent polymerase variant;
- introducing said plurality of nucleic acid plasmids individually into said plurality of host cells; and
- expressing said genes in said host cells to form template-independent polymerase variants encoded by said genes, wherein each host cell expresses a unique template-independent polymerase variant.

9. The method of claim 5, wherein said plasmid comprises a target oligonucleotide hybridization region comprising a sequence complementary to a portion of said target oligonucleotide.

* * * * *